(12) United States Patent
McDaniel et al.

(10) Patent No.: US 9,662,473 B2
(45) Date of Patent: *May 30, 2017

(54) DEFLECTABLE CATHETER WITH A HIGH MODULUS FIBER PULLER ELEMENT

(71) Applicant: Biosense Webster, Inc., Diamond Bar, CA (US)

(72) Inventors: Benjamin D. McDaniel, Irvine, CA (US); Dean M. Ponzi, Glendora, CA (US); Darrell Drysen, Sacramento, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 73 days.

This patent is subject to a terminal disclaimer.

(21) Appl. No.: 14/034,262

(22) Filed: Sep. 23, 2013

(65) Prior Publication Data

US 2014/0243743 A1    Aug. 28, 2014

Related U.S. Application Data

(63) Continuation of application No. 11/323,376, filed on Dec. 29, 2005, now Pat. No. 8,540,696.

(51) Int. Cl.
*A61M 25/01* (2006.01)
*A61B 18/14* (2006.01)
(Continued)

(52) U.S. Cl.
CPC ..... *A61M 25/0147* (2013.01); *A61B 18/1492* (2013.01); *A61M 25/00* (2013.01);
(Continued)

(58) Field of Classification Search
CPC ........ A61M 25/0147; A61M 2025/015; A61B 18/1492; A61B 5/6852
See application file for complete search history.

(56) References Cited

U.S. PATENT DOCUMENTS 4,960,134 A    10/1990 Webster, Jr.
RE34,502 E    1/1994 Webster, Jr.
(Continued)

FOREIGN PATENT DOCUMENTS

EP    0790066 A2    8/1997
EP    0839547 A1    5/1998
(Continued)

OTHER PUBLICATIONS

Extended European Search Report dated Feb. 4, 2008 for EP Application No. 06256600.5 (8 pages).
(Continued)

*Primary Examiner* — Laura Bouchelle
*Assistant Examiner* — Justin L Zamory
(74) *Attorney, Agent, or Firm* — Lewis Roca Rothgerber Christie LLP (57) ABSTRACT

A deflectable, catheter includes a catheter body, an intermediate section, a tip electrode and a control handle for deflecting the catheter by manipulation of a puller element that is made of a high modulus fiber material and extends through the catheter body and the intermediate section. The proximal end of the puller element is housed in the control handle and the distal end of the puller element is in a wrapped configuration and engages with a distal tip member or the intermediate section.

20 Claims, 4 Drawing Sheets (51) Int. Cl.
*A61M 25/00* (2006.01)
*A61B 5/00* (2006.01)

(52) U.S. Cl.
CPC ........ *A61B 5/6852* (2013.01); *A61M 25/0029* (2013.01); *A61M 2025/004* (2013.01); *A61M 2025/0034* (2013.01); *A61M 2025/015* (2013.01)

(56) References Cited

U.S. PATENT DOCUMENTS

| | | | |
|---|---|---|---|
| 5,540,703 A * | 7/1996 | Barker, Jr. | A61L 17/04 289/1.2 |
| 5,765,568 A | 6/1998 | Sweezer, Jr. et al. | |
| 5,827,278 A | 10/1998 | Webster, Jr. | |
| 6,074,351 A | 6/2000 | Houser et al. | |
| 6,602,242 B1 | 8/2003 | Fung et al. | |
| 6,648,875 B2 * | 11/2003 | Simpson | A61M 25/0136 600/585 |
| 6,905,476 B2 | 6/2005 | Ponzi | |
| 7,048,711 B2 * | 5/2006 | Rosenman | A61M 25/0014 604/95.04 |
| 7,377,906 B2 | 5/2008 | Selkee | |
| 7,594,903 B2 | 9/2009 | Webler et al. | |
| 2002/0165485 A1 | 11/2002 | Simpson et al. | |
| 2003/0004493 A1 | 1/2003 | Casey et al. | |
| 2003/0135199 A1 | 7/2003 | Rosenman et al. | |
| 2003/0187396 A1 | 10/2003 | Ponzi | |
| 2004/0059288 A1 | 3/2004 | Webler et al. | |
| 2004/0193032 A1 | 9/2004 | Mogul | |
| 2004/0225256 A1 | 11/2004 | Ponzi et al. | |
| 2005/0070844 A1 | 3/2005 | Chow et al. | |
| 2005/0277875 A1 * | 12/2005 | Selkee | A61M 25/0147 604/95.04 |
| 2006/0184106 A1 | 8/2006 | McDaniel et al. | |
| 2006/0264820 A1 | 11/2006 | Ponzi et al. | |
| 2007/0156132 A1 | 7/2007 | Drysen | |
| 2008/0027440 A1 | 1/2008 | Marissen et al. | |

FOREIGN PATENT DOCUMENTS

| | | |
|---|---|---|
| EP | 1046406 A2 | 10/2000 |
| EP | 1108441 A2 | 6/2001 |
| JP | 10-501159 A | 2/1998 |
| JP | 11-76258 | 3/1999 |
| WO | WO 96/40344 A1 | 12/1996 |

OTHER PUBLICATIONS

Extended European Search Report dated Mar. 14, 2011 for EP Application No. 10187626.6 (8 pages).

JP Notification of Reasons for Refusal (English translation) mailed Nov. 1, 2011, issued in JP Application No. 2006-355458, 3 pages.

* cited by examiner

DEFLECTABLE CATHETER WITH A HIGH MODULUS FIBER PULLER ELEMENT

CROSS-REFERENCE TO RELATED APPLICATION(S)

This application is a continuation of U.S. patent application Ser. No. 11/323,376, filed Dec. 29, 2005, the entire content of which is incorporated herein.

FIELD OF INVENTION

The invention is directed to a deflectable catheter, in particular, a deflectable catheter with puller element.

BACKGROUND

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Deflectable catheters are generally well-known. A convention catheter has a control handle with a housing having a piston chamber at its distal end. A piston is mounted in the piston chamber and is afforded lengthwise movement. The proximal end of the catheter body is attached to the piston. A puller wire is attached to the housing and extends through the piston and through the catheter body. The distal end of the puller wire is anchored in the intermediate section of the catheter. In this arrangement, lengthwise movement of the piston relative to the housing results in deflection of the catheter intermediate section.

The puller wire is typically made of a single, non-stranded metal wire, such as stainless steel or Nitinol, and is coated with Teflon® or the like. The coating imparts lubricity to the puller wire so that it can slide freely within a compression coil extending through the catheter body. The puller wire typically has a diameter ranging from about 0.006 to about 0.010 inch.

A typical method of anchoring the puller wire to the intermediate section of the catheter is by fixedly attaching, e.g., crimping, an anchor to the distal end of the puller wire. The anchor is then welded in a blind hole in a tip electrode.

Alternatively, the distal end of the puller wire is secured to the distal section of the catheter tubing. A short piece of tubular stainless steel, e.g., hypodermic stock, is fitted over the distal end of the puller wire and crimped to fixedly secure the puller wire. The distal end of the tubular stainless steel is fixedly attached, e.g., by welding, to a stainless steel crosspiece, which fits into a notch formed in the outer wall of the tubing. The portion of the notch not occupied by the crosspiece is filled with glue, or the like, such as a polyurethane glue that is harder than the material of the flexible tubing. With conventional crimping methods, the cross-sectional area of the crimped portion of the puller wire can be significantly decreased, thereby excessively weakening the puller wire.

While these methods are generally effective in securing the distal end of the puller wire, both crimping and soldering tend to weaken the puller wire, thereby subjecting the puller wire to fatigue and premature breakage.

Another typical method of anchoring the puller wire to the intermediate section and the housing is to wrap the wire around an anchor pin. Thus, in general, when a puller wire is used in a wrapped configuration whether for anchoring its distal end, or even around a pulley in a control handle for greater throw in the deflection of the catheter, the puller wire tends to work-harden in a wrapped position, leading to a loss in elasticity and premature breakage.

Accordingly, there is a desire for an improved puller element that can be manipulated by conventional control handles for deflecting catheters and yet be suited for attachment at its distal end in a manner that causes less fatigue and premature wearing. It is also desirable that such improved puller element retain more of its elasticity during repeated use and have overall better durability for use with control handles that provide more throw or employ pulley mechanisms to manipulate deflection of the catheter.

SUMMARY OF THE INVENTION

In one embodiment of a deflectable catheter according to the invention, the catheter includes a catheter body, an intermediate section at the distal end of the catheter body, a distal tip member distal the intermediate section, and a control handle at the proximal end of the catheter body. Also included is a puller element made of a high modulus fiber material and having proximal and distal ends, which extends through the catheter body. The proximal end of the puller element is housed in the control handle and the distal end of the puller element is in a wrapped configuration that engages with the distal tip member. Manipulation of the control handle results in movement of the puller element to deflect the intermediate section. The distal tip member may be, for example, a tip electrode. In one embodiment, the wrapped configuration of the puller element engages the intermediate section rather than the distal tip member.

In some embodiments, the deflectable catheter also includes a mechanical stop on the distal tip member, such as a clamp around the puller element, a protrusion extending from the distal tip member, an opening in at least a portion of the distal tip member through which the puller element extends, and/or a mold surrounding the puller element and the distal tip member. The mechanical stop could alternatively include an adhesive on the puller element and the intermediate section, and/or a groove on the intermediate section.

In some embodiments, the engagement of the wrapped configuration can be the puller element tied or wrapped around at least a portion of the distal tip member or around the mechanical stop. The engagement of the wrapped configuration may also include a knot in the distal end of the puller element in contact with an opening or channel.

The high modulus fiber material may be nonconductive and/or substantially nonstretching. In one embodiment, the high modulus fiber material is braided. The high modulus fiber material can be, for example, a polymeric material, High Molecular Density Polyethylene, a melt spun liquid crystal polymer fiber rope, or a spun para-aramid fiber polymer, or a high strength ceramic fiber. In some embodiments, the high modulus fiber material has a tensile strength in a range of about 300 ksi (2,000 MPa) to 1,500 ksi (10,400 MPa), more preferably around 450 ksi (3,100 MPa), and/or a tensile modulus in the range of about 5,000 ksi (35,000 MPa) to about 20,000 ksi (140,000 MPa), more preferably about 9,750 ksi (68,000 MPa).

DETAILED DESCRIPTION

Figure 1:
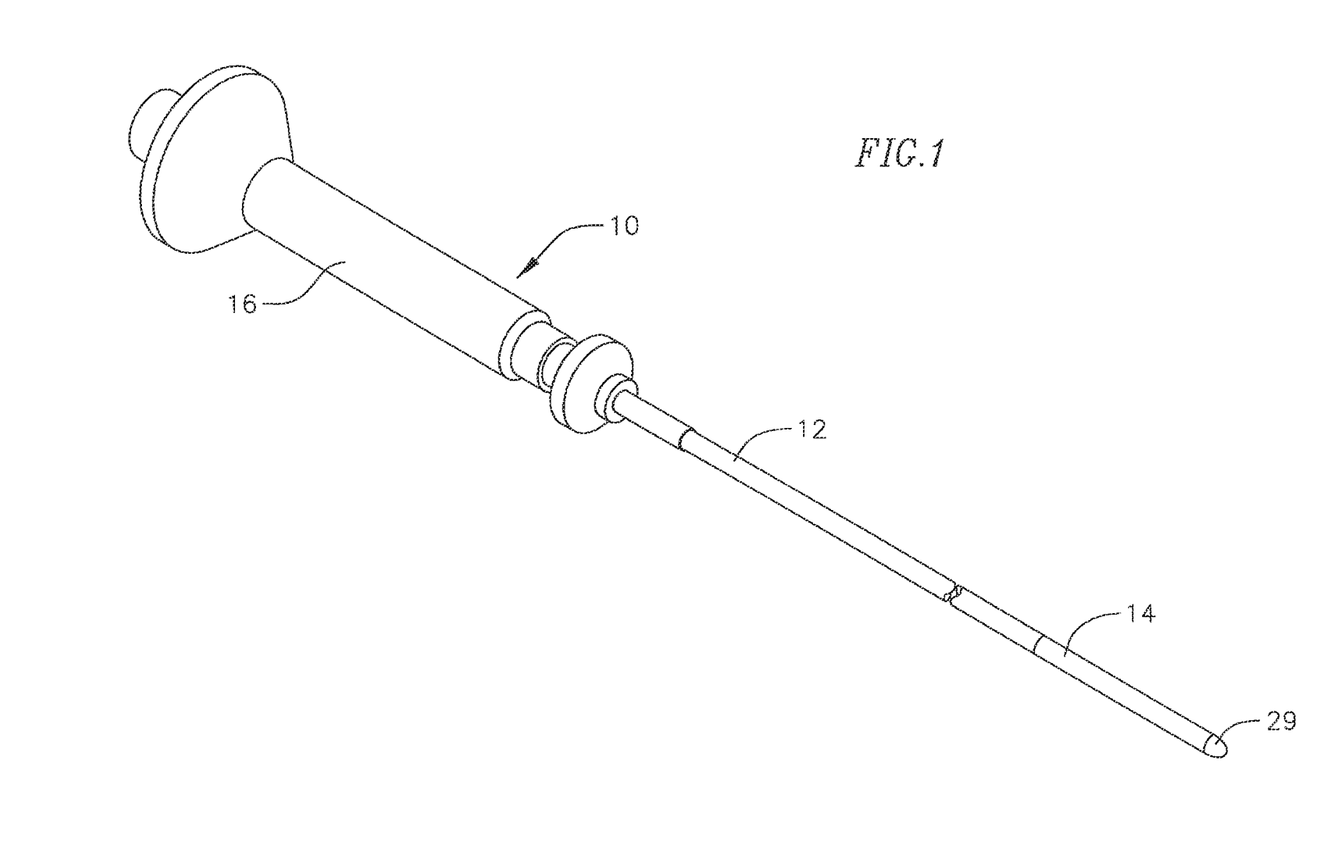
FIG. 1 is a side view showing a first embodiment of a catheter constructed in accordance with the present invention.

One embodiment of a deflectable electrode catheter constructed in accordance with the present invention is shown in FIGS. 1-5. In FIG. 1, the catheter 10 comprises an elongated catheter body 12, a deflectable intermediate section 14 distal the catheter body, a tip electrode 29 at a distal end of the intermediate section and a control handle 16 at a proximal end of the catheter body.

The overall length and diameter of the catheter may vary according to the application. A presently preferred catheter has an overall length of about 48 inches and an outer diameter of about 0.09 inches.

Figure 2:
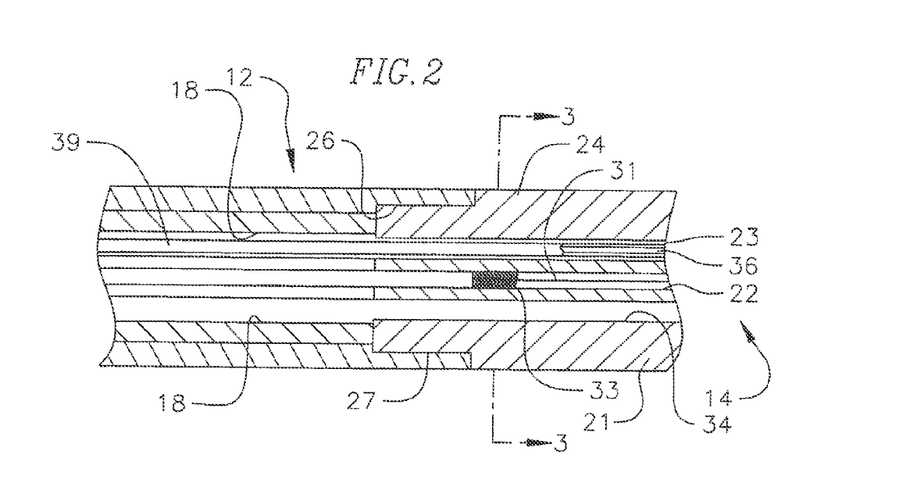
FIG. 2 is a side cross-sectional view of an embodiment of a junction of a catheter body and an intermediate section.

With reference to FIG. 2, the catheter body 12 comprises an elongated tubular construction having a central lumen 18. In one preferred embodiment, the lumen has a diameter of about 0.018 inch. The catheter body 12 is made of any suitable non-toxic material such as polyurethane. The catheter body 12 is preferably reinforced with at least one layer of a braided mesh of stainless steel or the like to increase its torsional stiffness. Extending through the single lumen 18 of the catheter body 12 are a lead wire 36 and a compression coil 33 through which a puller element 31, e.g., a puller tensile member, extends. While the catheter body 12 may be a multi-lumen body, a single lumen catheter body may be preferred with certain applications over a multi-lumen body because it has been found that the single lumen body permits better tip control when rotating the catheter. The single lumen permits the lead wire and the puller element surrounded by the compression coil and other components such as an electromagnetic sensor cable and/or an infusion tube to float freely within the catheter body. If such wires and tube were restricted within multiple lumens, they tend to build up energy when the handle is rotated, resulting in the catheter body having a tendency to rotate back if, for example, the handle is released, or if bent around a curve, to flip over, either of which are undesirable performance characteristics.

With reference to FIGS. 2-4A, the intermediate section 14 comprises a short section of flexible multi-lumen tubing 21. In the illustrated embodiment, a first lumen 23 carries one or more lead wires 36 and any other components (e.g., thermocouple wires for monitoring tissue temperature) extending along the catheter. A second lumen 22 carries the puller tensile member 31. A third lumen 34 is available to carry an electromagnetic sensor cable where an electromagnetic location sensor is carried in or near the distal tip member. As understood by one of ordinary skill in the art, these lumens are interchangeable so long as the puller tensile member extends through a lumen that is offset from the central axis of the tubing to facilitate deflection of the intermediate section when the tensile member is drawn distally, or otherwise manipulated by the control handle. Moreover, it is understood that any additional lumens may be used for fluid passage and/or carry an irrigation tube for supplying fluid to the tip electrode 29. Thus, the number of lumens or the size of each lumen is not critical, so long as it is sufficient to house the lead wires, puller tensile member, electromagnetic sensor cable, thermal sensors and/or irrigation tube(s) depending on the embodiment.

Figure 3:
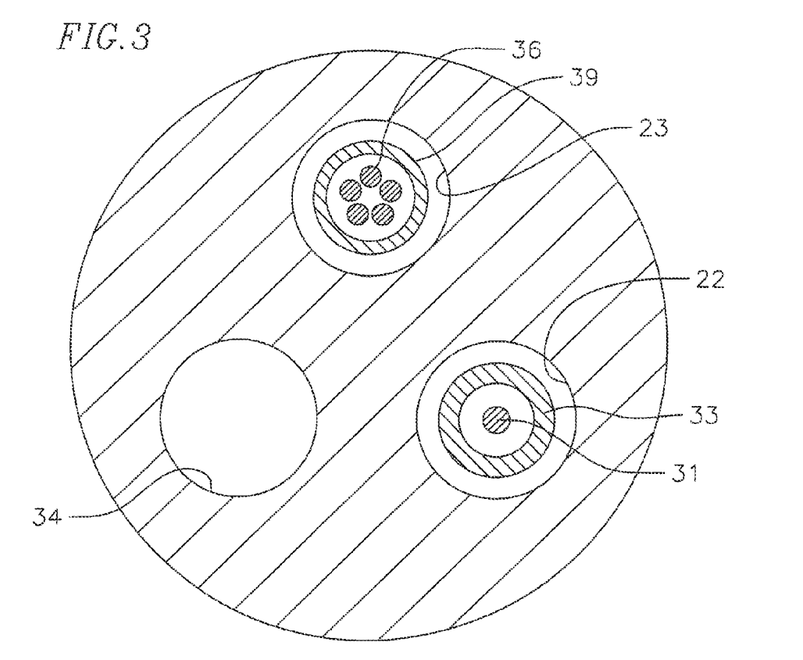
FIG. 3 is a longitudinal cross-sectional view of the intermediate section of FIG. 2 taken along line 3-3.
Figure 4A:
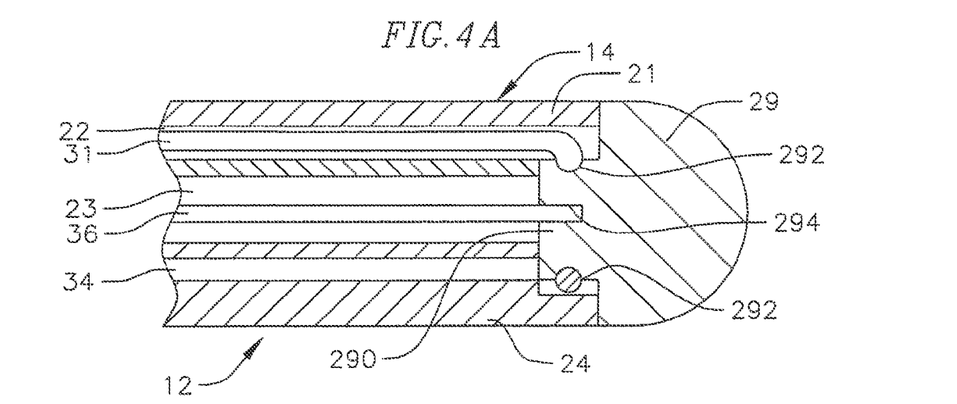
FIG. 4A is a side cross-sectional view of an embodiment of the intermediate section and a distal tip member.

The tubing 21 is made of a suitable material and is preferably more flexible than the catheter body 12. A presently preferred material for the intermediate section 14 is polyurethane. The intermediate section 14 is preferably reinforced with a metallic braided mesh 24 similar to that on the catheter body 12 to impart the same high torque characteristics without appreciably increasing its bending stiffness. The tip electrode 29 is at the distal end of the intermediate section.

The diameter of the intermediate section 14 is preferably the same as or slightly smaller than that of the catheter body 12. In a preferred embodiment, the diameter of the intermediate section is about 0.08-0.09 inches and the length is about 3 inches.

A preferred means for attaching the intermediate section 14 to the catheter body 12 is illustrated in FIG. 2. The proximal end of the intermediate section 14 comprises an outer circumferential notch 26 and the distal end of the catheter body 12 comprises an inner circumferential notch 27. The notches 26 and 27 are sized such that the proximal end of the intermediate section 14 fits snugly into the distal end of the catheter body 12. The intermediate section 14 is then fixedly attached to the catheter body by polyurethane glue or the like, creating a seam on the outer surface of the catheter at the junction between the intermediate section 14 and the catheter body 12.

The tip electrode 29 is connected to the lead wire 36 which extend through the central lumen 18 of the catheter body 12 and the first lumen 23 of the intermediate section 14. As better shown in FIGS. 2 and 3, the portion of the lead wire 36 and portions of any other lead wires that may be connected to ring electrodes carried on the intermediate section 14, extending through the central lumen 18 of the catheter body 12, control handle 16 and the intermediate section 14 are enclosed within a protective, nonconducting sheath 39, which can be made of any suitable material, preferably polyimide.

The proximal ends of lead wires 36 extend through the control handle and are connected to an appropriate jack or other connector which can be plugged into or otherwise connected to a suitable monitor or other electrophysiological equipment.

The puller tensile member 31 extends from the control handle 16 through the central lumen 18 in the catheter body 12 and into the second lumen 22 of the intermediate section 14. The puller tensile member has a diameter preferably from about 0.006 to about 0.010 inch.

With reference to FIG. 2, within the catheter body 12, there is provided a compression coil 33 extending through the lumen 18 in surrounding relation to the puller tensile member 31. The compression coil 33 is made of a suitable metal, e.g., stainless steel, which is tightly wound on itself to provide flexibility, i.e., bending, but to resist compression. The inner diameter of the compression coil 33 is selected to be slightly larger than the diameter of the puller tensile member 31. For example, when the puller tensile member 31 has a diameter of about 0.007 inch, a compression coil 33 having an inner diameter of about 0.008 inch is presently preferred. The outer diameter of the compression coil 33 is likewise slightly smaller than the diameter of the lumen 18 through which it extends. For example, if the central lumen 18 has a diameter of about 0.018 inch, the compression coil 33 preferably has an outer diameter of about 0.017 inch.

The distal end of the compression coil 33 could also be located in the proximal portion of the intermediate section 14 rather at the distal end of the catheter body 12. Such an embodiment provides added support to the juncture of the catheter body 12 and intermediate section 14. In accordance with one embodiment of the present invention, the puller tensile member 31 has a wrapped configuration at its distal end that is anchored to the distal tip electrode 29 mounted on the distal end of the intermediate section. As shown in the embodiment of FIG. 4A, the tip electrode 29 has at its proximal end a stem 290 to which the wrapped configuration of the puller tensile member is anchored. To that end, the proximal end of the tip electrode is notched circumferentially to form the stem, which fits inside a cored distal end of the tubing of the intermediate section and is bonded thereto by polyurethane glue or the like. In one embodiment (not shown), the tip electrode 29 has a total length of about 7 mm, with the stem having a length of about 3.5 mm (i.e., about half the total length of the tip electrode. The distal end of the tip electrode 29 is generally solid with a blind hole 294 to receive a distal end of a lead wire 36 for the tip electrode 29. Anchoring the puller tensile member 31 to the tip electrode 29 serves to secure the tip electrode and enable deflection of the intermediate section 14 through its entire length. To secure the distal end of the tensile member 31 to the stem of the tip electrode 29, the stem 290 may be configured with a variety of structural elements to engage the tensile member. As shown in FIG. 4A, one embodiment includes a mechanical stop in the form of a circumferential groove 292. The distal end of the puller element 31 that extends from the second lumen 22 of the tubing of the intermediate section is wrapped around the stem 290 and sits within the circumferential groove 292. Although the wrapped configuration of the tensile member 31 is shown in this embodiment to curve entirely around the stem, any suitable wrapped configuration, such as, for example, forming an opened or closed fold, wind, loop, or curve, is also within the scope of the invention. The puller tensile member 31, in this embodiment, is fastened to the stem 290 in a slip-knot at its distal end to engage the tip electrode. The wrapped portion of the puller tensile member 31 and the slip knot may be further bonded to the stem by polyurethane glue or the like when the tip electrode is inserted in the cored distal end of the tubing and bonded. Thus, as the puller tensile member 31 is drawn in the proximal direction, the intermediate section which carries the tip electrode at its distal end is deflected toward the side of the tubing of the second lumen 22 carrying the puller tensile member.

Figure 4B:
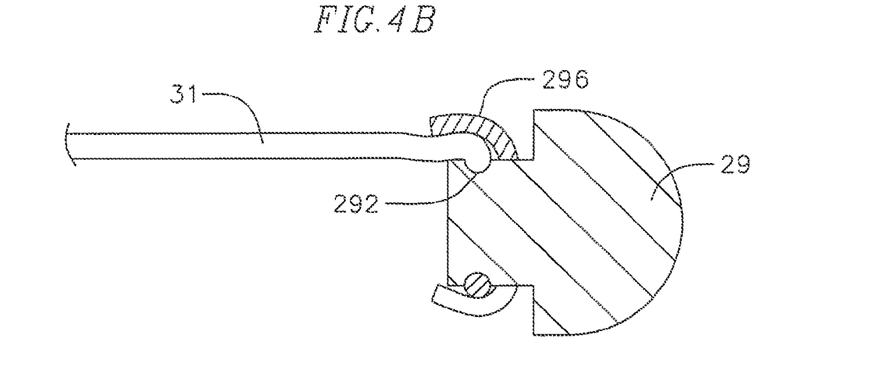
FIG. 4B is a simplified side cross-sectional view of another embodiment of the distal tip member and a puller element anchored thereto according to the invention.

In an alternative embodiment, as shown in FIG. 4B, the puller tensile member 31 is in a wrapped configuration within the groove 292 of the stem 290, but further fixed to the stem 290 by a clamp or a ring 296 that squeezes the puller tensile member 31 into the groove 292 and fixedly retains the puller tensile member in the groove. The clamp 296 may be made of any suitable material, such as metal, plastic, ceramic, etc. An adhesive, or mold may also be used in place of the clamp 296 to hold the puller tensile member 31 in the groove 292.

Figure 4C:
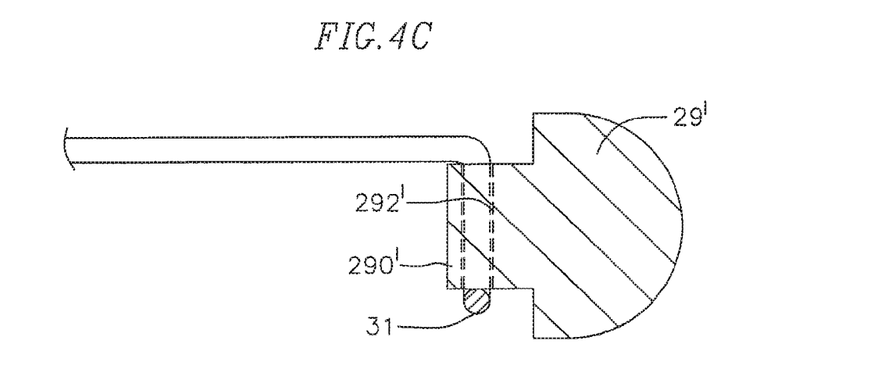
FIG. 4C is a simplified side cross-sectional view of another embodiment of the distal tip member and the puller element anchored thereto according to the invention.

Referring to FIG. 4C, this embodiment includes a stem 290' of a tip electrode 29', the stem 290' having a channel 292' drilled therethrough, through which the puller tensile member 31 extends. The wrapped configuration of the puller tensile member 31 is formed by tying the distal end in any fashion, e.g., in a slip-knot around the stem, or a knot with itself that is sized larger than the channel to prevent the knot from entering the channel when the puller tensile member is drawn proximally.

Figure 4D:
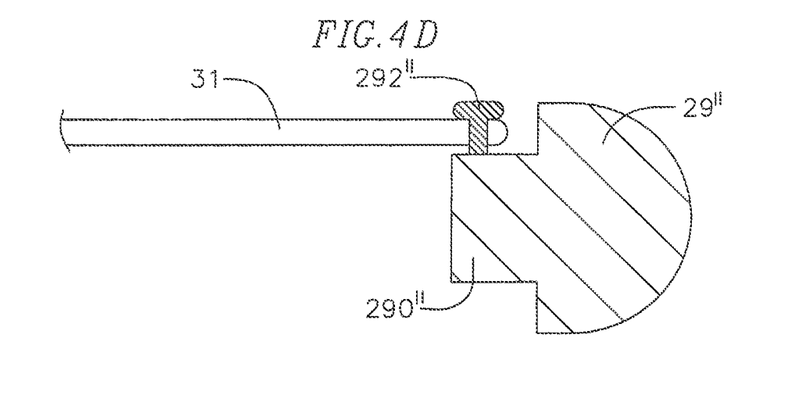
FIG. 4D is a simplified side cross-sectional view of another embodiment of the distal tip member and the puller element anchored thereto according to the invention.
Figure 4E:
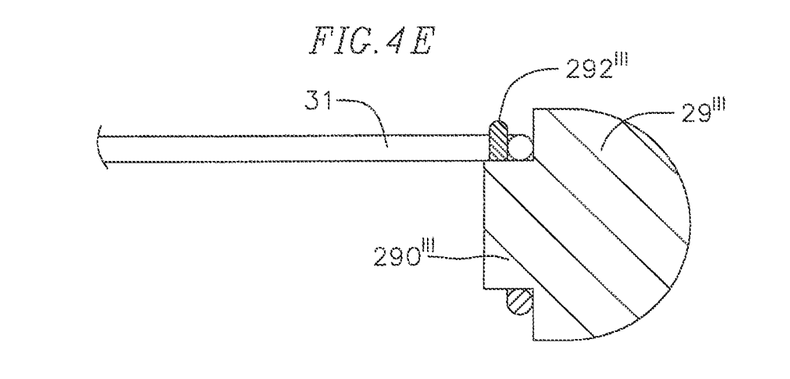
FIG. 4E is a simplified side cross-sectional view of another embodiment of the distal tip member and the puller element anchored thereto according to the invention.

In the embodiment shown in FIG. 4D, the stem 290" of the tip electrode 29" includes a mechanical stop in the form of a projecting pin 292", around which the puller tensile member 31 is wrapped and fixed through suitable means. In the embodiment shown in FIG. 4E shows the puller tensile member 31 wrapped around the stem 290''' of the tip electrode 29''' and obstructed from slipping off the stem 290''' by a mechanical stop on the stem 290''' in the form of a protrusion 292'''. The protrusion 292''' is shown projecting directly out of the stem 290''' at a 90 degree angle, but any angle or configuration capable of preventing slippage of the pulling element 31 off of the stem is also within the scope of the invention.

Figure 5:
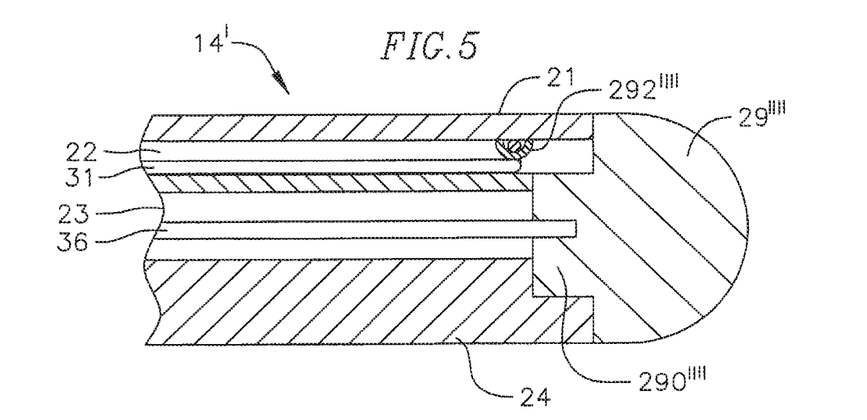
FIG. 5 is a side cross-sectional view of another embodiment of the puller element anchored to the intermediate section according to the invention.

As shown in FIG. 5, the mechanical stop in the form of a loop 292'''' can also be located on the interior side wall of the intermediate section 14' as opposed to the stem 290'''' of the tip electrode 29'''. The puller tensile member 31 that extends through the lumen 22 is wrapped through the loop 292''' and the wrapped configuration of the puller tensile member 31 engages the loop such that movement of the puller tensile member 31 in the proximal direction bends the flexible tubing 21, as described above.

In accordance with a feature of the invention, the puller tensile member 31 is made of a high modulus fiber material, preferably having a tensile modulus substantially in the range of 5,000 ksi (35,000 MPa) to about 20,000 ksi (140,000 MPa), more preferably about 9,750 ksi (68,000 MPa), such as High Molecular Density Polyethylene (e.g., Spectra™ or Dyneema™), a spun paraaramid fiber polymer (e.g., Kevlar™) or a melt spun liquid crystal polymer fiber rope (e.g., Vectran™), or a high strength ceramic fiber (e.g., Nextel™). These materials tend to be flexible, providing suitable durability when used in wrapped engagement with the tip electrode or around pulleys in the control handle for increased throw. Further, they are substantially non-stretching, which increases the responsiveness to the manipulation of the control handle, and nonmagnetic so that they generally appear transparent to an MRI. The low density of the material causes it to be generally transparent to an x-ray machine. The materials can also be nonconductive to avoid shorting. Vectran™, for example, has high strength, high abrasion resistance, is an electrical insulator, nonmagnetic, is polymeric, and has low elongation under a load.

Preferably, the puller tensile member 31 has a tensile strength ranging between about 300 ksi (2,000 MPa) to 1,500 ksi (10,400 MPa), more preferably around 450 ksi (3,100 MPa). This would allow the puller tensile member 31 to have a higher strength than conventional steel puller wires as well as a reduced cross-section. In one embodiment, the high modulus fiber material is braided.

Referring to FIGS. 1-5, any suitable control handle 16 which can control longitudinal movement of the puller tensile member 31 relative to the catheter body may be used. A preferred control handle 16, as shown in FIG. 1, is described in U.S. Pat. No. 4,960,134 and Re U.S. Pat. No. 34,502, the entire disclosures of which are incorporated herein by reference. The handle has a piston 19 that controls the longitudinal movement of the puller tensile member 31. The puller tensile member 31 may be in a wrapped configuration that engages with the piston at its proximal end in a manner similar to its fixation to the intermediate section, discussed above. In the illustrated embodiment, proximal movement of the puller tensile member with respect to the catheter body deflects the intermediate section and distal movement of the puller tensile member with respect to the catheter body returns the intermediate section to its nondeflected resting shape. Due to the advantages provided by the puller tensile member of the present invention as mentioned above, the present invention is particularly well suited for control handles that use pulleys and the like to provide greater throw in deflection of the catheter, such as described in U.S. application Ser. No. 10/871,691, filed Jun. 15, 2004, the entire disclosure of which is incorporated by reference herein.

It is understood that any mechanism for attaching the proximal end of the puller tensile member to the control handle may be used.

In the embodiment described above, the compression coil is preferably covered by a non-conductive sheath to prevent electrical contact with the lead wires. Moreover, a tunnel is formed in each of the glue joints securing the proximal and distal ends of the compression coil to the catheter body. The tunnels provide means for passage of the electrode lead wires through the glue joints. Such a tunnel may be formed, for example, by short pieces of polyimide tubing or the like.

It is also understood by one of ordinary skill in the art that the present invention is not limited to a catheter with a single puller element, but may include two or more puller element for bi-directional deflection or more complex deflection configurations, such as S-type deflection or catheters with a preformed or preshaped distal end having combinations of straight and curved portions. Moreover, one of ordinary skill in the art understands that the catheter of the present invention is adaptable to carry an electromagnetic location sensor at or near the distal end of the intermediate section, whereupon its sensor cable is carried in the third lumen 34 of the intermediate section and the central 18 of the catheter body. Similarly the catheter of the present invention is adaptable to provide irrigation and infusion at the distal end of the intermediate section through the distal tip member. To that end, infusion/irrigation fluids may be transported via a tube segment extending in the central lumen 18 of the catheter body 12 and the third lumen 34 of the intermediate section 14, or a fourth lumen in the intermediate section 14, as desired. Suitable adaptations and embodiments are disclosed in U.S. Pat. No. 6,602,242, the entire disclosure of which is hereby incorporated.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A deflectable catheter comprising:
  a catheter body;
  an intermediate section at a distal end of the catheter body;
  a distal tip electrode distal the intermediate section, the distal tip electrode comprising a stem with an outer circumferential surface;
  a control handle at a proximal end of the catheter body; and
  a puller element comprising a high modulus fiber material and having proximal and distal ends, the puller element extending through the catheter body and the intermediate section, wherein the proximal end of the puller element is housed in the control handle and the distal end of the puller element has a wrapped configuration in engagement with the stem of the distal tip electrode, the wrapped configuration comprising:
    the distal end of the puller element wrapping around at least a portion of the outer circumference of the stem of the distal tip electrode, or
    the distal end of the puller element extending through a channel in the stem of the distal tip electrode and terminating in a knot that is larger than the channel, or
    the distal end of the puller element wrapping around a protrusion extending from the outer circumference of the stem of the distal tip electrode; and
  manipulation of the control handle results in movement of the puller element to deflect the intermediate section.

2. The deflectable catheter according to claim 1, further comprising means for anchoring the wrapped configuration to the distal tip electrode.

3. The deflectable catheter according to claim 1, further comprising a stop on the distal tip electrode or the puller element or both the distal tip electrode and the puller element.

4. The deflectable catheter according to claim 3, wherein the stop comprises a clamp on the puller element and the stem of the distal tip electrode.

5. The deflectable catheter according to claim 3, wherein the stop comprises a protrusion extending from the outer circumference of the stem of the distal tip electrode, the protrusion being configured to obstruct the wrapped configuration from slipping off the stem.

6. The deflectable catheter according to claim 3, wherein the stop comprises a mold on the puller element and the stem of the distal tip electrode.

7. The deflectable catheter according to claim 3, wherein the stop comprises an adhesive on the puller element and the stem of the distal tip electrode.

8. The deflectable catheter according to claim 1, wherein the wrapped configuration comprises the distal end of the puller element wrapping around at least the portion of the outer circumference of the stem of the distal tip electrode in a groove on the outer circumference of the stem of the distal tip electrode.

9. The deflectable catheter according to claim 1, wherein the engagement of the wrapped configuration comprises the distal end of the puller element tied to the distal tip electrode.

10. The deflectable catheter according to claim 1, wherein the high modulus fiber material is nonconductive.

11. The deflectable catheter according to claim 1, wherein the high modulus fiber material is generally nonstretching.

12. The deflectable catheter according to claim 1, wherein the high modulus fiber material is braided.

13. The deflectable catheter according to claim 1, wherein the high modulus fiber material comprises a polymeric material.

14. The deflectable catheter according to claim 1, wherein the high modulus fiber material comprises a ceramic material.

15. The deflectable catheter according to claim 1, wherein the high modulus fiber material comprises High Molecular Density Polyethylene.

16. The deflectable catheter according to claim 1, wherein the high modulus fiber material comprises a melt spun liquid crystal polymer fiber rope.

17. The deflectable catheter according to claim 1, wherein the high modulus fiber material comprises a spun para-aramid fiber polymer.

18. The deflectable catheter according to claim 1, wherein the high modulus fiber material has a tensile strength ranging between about 2,000 MPa and about 10,400 MPa.

19. The deflectable catheter according to claim 1, wherein the high modulus fiber material has a tensile modulus substantially in the range of about 35,000 MPa to about 140,000 MPa.

20. A deflectable catheter comprising:
a catheter body;
an intermediate section distal the catheter body;
a distal tip electrode distal the intermediate section, the distal tip electrode comprising a stem with an outer circumferential surface; and
a puller element comprising a high modulus fiber material and having proximal and distal ends, the puller element extending through the catheter body and the intermediate section, wherein the puller element has a wrapped configuration in engagement with the stem of the distal tip electrode, the wrapped configuration comprising:
the distal end of the puller element wrapping around at least a portion of the outer circumference of the stem of the distal tip electrode, or
the distal end of the puller element extending through a channel in the stem of the distal tip electrode and terminating in a knot that is larger than the channel, or
the distal end of the puller element wrapping around a protrusion extending from the outer circumference of the stem of the distal tip electrode.

* * * * *